United States Patent [19]

Kokubo

[11] Patent Number: 5,681,382
[45] Date of Patent: Oct. 28, 1997

[54] RAPIDLY SOLUBLE COATING COMPOSITION AND METHOD FOR PREPARING SAME

[75] Inventor: Hiroyasu Kokubo, Nakakubiki-gun, Japan

[73] Assignee: Shin-Etsu Chemical Co., Ltd., Japan

[21] Appl. No.: 699,054

[22] Filed: Aug. 9, 1996

[30] Foreign Application Priority Data

Aug. 22, 1995 [JP] Japan ................. 7-213561
Aug. 22, 1995 [JP] Japan ................. 7-213562

[51] Int. Cl.$^6$ ................................. C09D 101/28
[52] U.S. Cl. ................. 106/184.1; 106/194.2; 106/172.1
[58] Field of Search .................. 106/172.1, 184.1, 106/194.2

[56] References Cited

U.S. PATENT DOCUMENTS

| | | | |
|---|---|---|---|
| 2,322,013 | 6/1943 | Gilbert | 106/184.1 |
| 3,539,380 | 11/1970 | Johnson | 106/194.2 |
| 4,543,370 | 9/1985 | Porter et al. | 106/184.1 |
| 4,816,298 | 3/1989 | Alderman et al. | 106/194.2 |
| 5,393,333 | 2/1995 | Trouve | 106/194.2 |

*Primary Examiner*—David Brunsman
*Attorney, Agent, or Firm*—Parkhurst, Wendel & Burr, L.L.P.

[57] ABSTRACT

A plasticizer which is in a solid state at ordinary temperature and a pigment are added to and mixed with a coating base which consists of particulate hydroxypropyl methyl cellulose and/or methyl cellulose having an average particle size ranging from 200 to 1000 μm and whose content of particles having a particle size of not more than 75 μm is not more than 30% by weight. The resulting mixture is heated to a temperature of not less than the solidification point of the plasticizer to give a rapidly soluble coating composition. If the plasticizer is in a liquid state at ordinary temperature, a powdery pigment is added to and mixed with the foregoing coating base while spraying the liquid plasticizer on the resulting mixture to give a rapidly soluble coating composition.

7 Claims, No Drawings

RAPIDLY SOLUBLE COATING COMPOSITION AND METHOD FOR PREPARING SAME

BACKGROUND OF THE INVENTION

The present invention relates to a rapidly soluble coating composition which is applied onto tablets of, for instance, drugs to thus form an outer film thereon as well as a method for preparing the same.

Tablets of, for instance, drugs are coated with a water-soluble coating layer so that the user does not taste any bitterness in his mouth. In this respect, hydroxypropyl methyl cellulose has most widely been used as a base for a water-soluble film, i.e., a polymer serving as a coating base. Hydroxypropyl methyl cellulose is dissolved in water to give a coating solution and the coating solution is applied to desired tablets and then dried to form a water-soluble film thereon.

There had been used organic coating solutions at that time when the method for coating tablets with other films was, for the first time, developed (in the 1950's). The organic coating solution can be prepared, within a short period of time, by first dispersing, for instance, hydroxypropyl methyl cellulose in a poor solvent and then adding a good solvent thereto to thus dissolve the cellulose. However, there have been used aqueous coating solutions, since the beginning of the 1970's, each prepared by dissolving a coating base in water for the purpose of saving the production cost and preventing the environmental pollution.

A method for preparing such an aqueous coating solution comprises the steps of dispersing hydroxypropyl methyl cellulose or methyl cellulose in hot water and then cooling the dispersion to thus dissolve the cellulose. Alternatively, there has also been known another method for preparing such an aqueous coating solution which comprises introducing hydroxypropyl methyl cellulose or the like in water having ordinary temperature (on the order of 25° C.). However, the method which makes use of hot water requires a long period of time for the cooling step, while in the method using water having ordinary temperature, it takes several hours to one day till the coating base is completely dissolved in water.

If the preparation of such a coating solution requires a long period of time, microorganisms would develop and proliferate in the aqueous solution and this accordingly makes the storage of the aqueous coating solution quite difficult. In particular, if a coating solution is prepared on the weekend, microorganisms would often be proliferated therein at the beginning of the next week (i.e., on Monday). There has been known a method in which a preservative is added to such a coating solution as a means for preventing the proliferation of microorganisms, but the addition thereof is not preferred for the coating solution which is applied to drugs. For this reason, there has been desired for the development of a method for preparing an aqueous coating solution which permits the preparation of such a solution within a very short time to thus prevent any proliferation of microorganisms.

As a means for preparing a coating solution within a short period of time, there has been known a method which makes use of a specific dissolution apparatus such as a homomixer. However, this method requires too much expenses and results in the formation of a large quantity of foams.

As a still further means for preparing a coating solution within a short period of time, there has been known a method which makes use of a premix prepared by incorporating a pigment and a plasticizer and optionally a surfactant. Such premix products are roughly divided into solution type and powder type premixes. The solution type premix per se may be used as a coating solution or may be diluted with water prior to use as a coating solution. However, the solution type one is more expensive than those in situ prepared through mixing and it is necessary to change the color tone and the mixing ratio or composition depending on products and this accordingly makes the control of stockpile very complicated.

On the other hand, the term "powder type premix product" means a coating composition which is prepared by mixing a coating base with a pigment in advance and then adding a plasticizer and a surfactant to the mixture, as disclosed in Japanese Patent Application Publication No. 2-29655. In the powder type one, polyethylene glycol (PEG) added as a plasticizer permits the improvement of the coating base in its dispersibility and therefore, such a coating solution is in general prepared using water of ordinary temperature. However, the powder type premix is heterogeneous, pigment particles are easily recognized and they are often separated from the powder premix in a packaging container during transportation. U.S. Pat. No. 5,258,436 discloses a method for improving such heterogeneity of the powder type premix by lyophilizing an aqueous solution comprising a water-soluble cellulose acetate, a plasticizer and a pigment. This method permits the production of a premix product which is uniform and excellent in abilities of redispersion and solubilization, but this method requires too much expenses for the lyophilization. Moreover, the conditions for stirring should strictly be established in order to obtain a premix product exhibiting good dispersibility and solubility.

SUMMARY OF THE INVENTION

The present invention has been developed for the purpose of solving the foregoing problems associated with the conventional techniques and accordingly, it is an object of the present invention to provide a rapidly soluble coating composition which can rapidly be dissolved in an aqueous solvent and hardly causes separation of a pigment as well as a method for preparing the same.

The rapidly soluble coating composition according to the present invention which has been developed for accomplishing the foregoing object comprises a coating base which is particulate hydroxypropyl methyl cellulose and/or methyl cellulose having an average particle size ranging from 200 to 1000 μm and whose content of particles having a particle size of not more than 75 μm is not more than 30% by weight; a plasticizer; and a pigment.

If the plasticizer is a solid substance at ordinary temperature, the rapidly soluble coating composition is prepared by adding a solid plasticizer and a pigment to a coating base which consists of particulate hydroxypropyl methyl cellulose and/or methyl cellulose having an average particle size ranging from 200 to 1000 μm and whose content of particles having a particle size of not more than 75 μm is not more than 30% by weight and mixing them together and thereafter heating the resulting mixture to a temperature of not less than the solidification point of the plasticizer.

On the other hand, if the plasticizer is in a liquid state at ordinary temperature, the rapidly soluble coating composition is prepared by adding a powdery pigment, while spraying the liquid plasticizer, to a coating base which consists of particulate hydroxypropyl methyl cellulose and/or methyl cellulose having an average particle size ranging from 200 to 1000 μm and whose content of particles having a particle size of not more than 75 μm is not more than 30% by weight and mixing them together.

DETAILED EXPLANATION OF THE INVENTION

The plasticizer which is solid at ordinary temperature and which is added to the rapidly soluble coating composition of the present invention is preferably at least one member selected from the group consisting of polyethylene glycols having a weight-average molecular weight ranging from 950 to 25000. These plasticizers have a solidification temperature ranging from 35° to 40° C. for those having a weight-average molecular weight of 1000 and 56° to 64° C. for those having a weight-average molecular weight of 20000. As solid polyethylene glycols, preferred are powdery polyethylene glycols having an average particle size of not more than 500 μm. If commercially available powdery polyethylene glycol is incorporated into the composition, the resulting coating composition has poor extensibility upon melting with heating.

The plasticizer which is in a liquid state at ordinary temperature and which is added to the rapidly soluble coating composition of the present invention is preferably at least one member selected from the group consisting of polyethylene glycol having a weight-average molecular weight ranging from 190 to 630, propylene glycol, glycerin, triacetin and triethyl citrate. Among these, particularly preferred are polyethylene glycols which are highly water-soluble and have high surface activity and have an effect of preventing sticking during coating.

The concentrations of both solid and liquid plasticizers each preferably ranges from 5 to 30% by weight on the basis of the weight of the coating base. This is because if the concentration is less than 5% by weight, the pigment causes separation from the rapidly soluble coating composition, while if it exceeds 30% by weight, the plasticizer is liable to easily undergo precipitation through bleeding. A surfactant may arbitrarily be added to the plasticizer for the purpose of further improvement of the composition in the dispersibility. Examples of surfactants capable of being incorporated into the liquid plasticizers are non-ionic surfactant such as Tween 80, sucrose fatty acid esters and anionic surfactants such as sodium lauryl sulfate.

The coating base herein used is preferably hydroxypropyl methyl cellulose and methyl cellulose. In particular, hydroxypropyl methyl cellulose can most widely be used in the invention.

The average particle size of the coating base preferably ranges from 200 to 1000 μm. If it is less than 200 μm, the coating base exhibits a reduced dispersion effect, undergoes the formation of agglomerates during dissolution and therefore it takes a long time in order to completely dissolve the same. On the other hand, if it exceeds 1000 μm, the base exhibits good dispersibility, but complete dissolution of each particle requires a long period of time.

The content of particles having a particle size of not more than 75 μm included in the coating base is preferably not more than 30% by weight. If the content exceeds 30% by weight, the coating base may have a high possibility of forming agglomerates even if the average particle size is not less than 200 μm and therefore, the dissolution thereof requires a long time. The particle size of the coating base may be controlled by properly adjusting the conditions for pulverization and classification during granulation or production steps.

The viscosity of a 2% by weight aqueous solution of the coating base ranges from 2 to 60 cP and particularly preferably 2 to 20 cP. If the viscosity is less than 2 cP, the concentration of the resulting coating solution is quite low and accordingly, it takes a long time for coating, for instance, drugs. On the other hand, if it exceeds 60 cP, the concentration of the resulting coating solution is extremely high and this makes, difficult, the spraying of the solution on drugs or the like using an apparatus or the like.

The pigment herein used is preferably powdery titanium oxide and/or iron oxide, which have high densities and easily cause separation.

The concentration of the pigment preferably ranges from 1 to 30% by weight on the basis of the weight of the coating base. This is because if it is less than 1% by weight, the pigment does not ensure a high effect of heat-treatment, while if it exceeds 30% by weight, the pigment easily causes separation. In addition, a lake dye may be incorporated into the coating solution in addition to the foregoing pigment, like the usual premix products. Alternatively, other food dyes may be incorporated into the pigment.

When mixing the coating base, the plasticizer and the pigment in the method according to the present invention, a mixer is preferably used. Examples of such mixers are a conical type mixer, a twin-cylinder mixer and a high-speed blender, which are provided with a jacket for heating the contents thereof. If using hot air as a heating medium, a fluidized bed mixer may be used. An apparatus such as a high-speed stirring granulator is preferably used, which has high stirring and mixing power.

The resulting rapidly soluble coating composition can be dissolved in water to form a coating solution. The coating solution is sprayed on drugs using a coating device, followed by drying the sprayed coating solution to form a film covering the drugs. The coating solution may comprise other pharmaceutically acceptable additives such as a surface tack eliminator. Examples of coating devices usable herein are a fluidized bed coating device, a pan coating device and a flow-through rotational drum type coating device.

The rapidly soluble coating composition according to the present invention can rapidly be dissolved in water without using any particular device for dissolution to thus immediately give an aqueous coating solution. Moreover, a fixed color tone can always be reproduced since the coating solution does not cause any separation and segregation of the pigment. The aqueous coating solution is prepared immediately before the application thereof onto drugs and therefore, any problem does not arise, such as a decrease in the shelf life and proliferation of microorganisms during storage.

The present invention will hereinafter be described in more detail with reference to the following working Examples, but the present invention is by no means limited to the specific working Examples which may properly be changed or modified.

Examples 1 to 8 and Comparative Examples 1 to 3 relate to rapidly soluble coating solutions containing solid plasticizers, while Examples 9 to 16 and Comparative Examples 4 to 8 relate to rapidly soluble coating solutions containing liquid plasticizers.

EXAMPLE 1

There were introduced, into a high-speed stirring granulator, 500 g of hydroxypropyl methyl cellulose having an average particle size of 373 μm and the following particle size distribution: ≧1000 μm 0.6%; 710–1000 μm 4.4%;

500~710 μm 29.8%; 355~500 μm 25.2%; 250~355 μm 14.8%; 180~250 μm 6.8%; and ≦180 μm 18.4% and whose viscosity as determined using a 2% by weight aqueous solution is 6 cP, 80 g of titanium oxide (A-110 available from Sakai Chemical Industries, Ltd.) and 80 g of polyethylene glycol 6000 (Macrogol 6000P; weight-average molecular weight: 7300~9300; solidification point: 56°~61° C.; available from Nippon Oil and Fats Co., Ltd.). Then these ingredients were mixed for 10 minutes with stirring and heating the jacket to 70° C. to give a rapidly soluble coating composition.

Purified water (188 ml) was added to an 8 oz bottle, then stirring blades were fitted to the bottle and the bottle was then immersed in a thermostatic chamber maintained at a temperature of 25° C. More specifically, at an instance when the temperature of the purified water reached 25° C., 12 g of the sample (rapidly soluble coating composition) was added to the purified water at a time while stirring at 500 rpm and the stirring operation was continued till the composition was completely dissolved therein. After the undissolved particles or agglomerates present therein disappeared, the resulting solution was passed through a screen of 18 mesh (850 μm) and the screen was inspected for the presence of residues. The solubilization time of the composition was defined to be the time required till any residue was not observed on the screen. In this case, the solubilization time was found to be 8 minutes.

The rapidly soluble coating composition was roughly divided into 3 kinds of groups each having the following particle size distribution: 24~30 mesh; 42~60 mesh; and 100 mesh pass, through classification and the content of titanium oxide present in each group was determined. The results thus obtained are listed in Table 1. In this regard, the shaking times for the classification were set at 20 minutes and one hour.

EXAMPLE 2

The same procedures used in Example 1 were repeated except for using hydroxypropyl methyl cellulose having an average particle size of 504 μm, the following particle size distribution: ≧1000 μm 1.0%; 710~1000 μm 18.5%; 500~710 μm 42.5%; 355~500 μm 18.5%; 250~355 μm 7.0%; 180~250 μm 3.8%; and ≦180 μm 8.7% and whose viscosity as determined using a 2% by weight aqueous solution is 3 cP to thus prepare a rapidly soluble coating composition and to determine the solubilization time. In this case the latter was found to be 4 minutes.

The resulting rapidly soluble coating composition was roughly divided into three groups each having the following particle size distribution: 24~30 mesh; 42~60 mesh; and 100 mesh pass through classification, in the same manner used in Example 1, and the content of titanium oxide present in each group was determined. The results thus obtained are listed in Table 1.

EXAMPLE 3

The same procedures used in Example 1 were repeated except for using hydroxypropyl methyl cellulose having an average particle size of 429 μm, the following particle size distribution: ≧1000 μm 0.4%; 710~1000 μm 14.0%; 500~710 μm 37.4%; 355~500 μm 20.6%; 250~355 μm 7.0%; 180~250 μm 4.6%; and ≦180 μm 16.0% and whose viscosity as determined using a 2% by weight aqueous solution is 15 cP to thus prepare a rapidly soluble coating composition and to determine the solubilization time. The latter was found to be 19 minutes.

The resulting rapidly soluble coating composition was roughly divided into three groups each having the following particle size distribution: 24~30 mesh; 42~60 mesh; and 100 mesh pass through classification, in the same manner used in Example 1, and the content of titanium oxide present in each group was determined. The results thus obtained are listed in Table 1.

EXAMPLE 4

The same procedures used in Example 1 were repeated except for using hydroxypropyl methyl cellulose having an average particle size of 255 μm, the following particle size distribution: ≧1000 μm 1.0%; 710~1000 μm 4.5%; 500~710 μm 11.0%; 355~500 μm 16.2%; 250~355 μm 17.9%; 180~250 μm 15.6%; and ≦180 μm 16.6% and whose viscosity as determined using a 2% by weight aqueous solution is 15 cP to thus prepare a rapidly soluble coating composition and to determine the solubilization time. The latter was found to be 18 minutes.

The resulting rapidly soluble coating composition was roughly divided into three groups each having the following particle size distribution: 24~30 mesh; 42~60 mesh; and 100 mesh pass through classification, in the same manner used in Example 1, and the content of titanium oxide present in each group was determined. The results thus obtained are listed in Table 1.

EXAMPLE 5

The same procedures used in Example 1 were repeated except for using 40 g of polyethylene glycol 20000 (Macrogol 20000: weight-average molecular weight 15000 to 25000; solidification point 56° to 64° C., available from Nippon Oil and Fats Co., Ltd.) to thus prepare a rapidly soluble coating composition and to determine the solubilization time. The latter was found to be 12 minutes.

The resulting rapidly soluble coating composition was roughly divided into three groups each having the following particle size distribution: 24~30 mesh; 42~60 mesh; and 100 mesh pass through classification, in the same manner used in Example 1, and the content of titanium oxide present in each group was determined. The results thus obtained are listed in Table 1.

EXAMPLE 6

The same procedures used in Example 1 were repeated except for using 125 g of polyethylene glycol 4000 (Macrogol 4000: weight-average molecular weight 2600 to 3800; solidification point 53° to 57° C., available from Nippon Oil and Fats Co., Ltd.) to thus prepare a rapidly soluble coating composition and to determine the solubilization time. The latter was found to be 6 minutes.

The resulting rapidly soluble coating composition was roughly divided into three groups each having the following particle size distribution: 24~30 mesh; 42~60 mesh; and 100 mesh pass through classification, in the same manner used in Example 1, and the content of titanium oxide present in each group was determined. The results thus obtained are listed in Table 1.

EXAMPLE 7

The same procedures used in Example 1 were repeated except for using 40 g of titanium oxide (A-110 available from Sakai Chemical Industries., Ltd.) as the pigment component to thus prepare a rapidly soluble coating composition and to determine the solubilization time. The latter was found to be 10 minutes.

The resulting rapidly soluble coating composition was roughly divided into three groups each having the following particle size distribution: 24~30 mesh; 42~60 mesh; and 100 mesh pass through classification, in the same manner used in Example 1, and the content of titanium oxide present in each group was determined. The results thus obtained are listed in Table 1.

EXAMPLE 8

The same procedures used in Example 1 were repeated except for using 125 g of titanium oxide (A-110 available from Sakai Chemical Industries., Ltd.) as the pigment component to thus prepare a rapidly soluble coating composition and to determine the solubilization time. The latter was found to be 8 minutes.

The resulting rapidly soluble coating composition was roughly divided into three groups each having the following particle size distribution: 24~30 mesh; 42~60 mesh; and 100 mesh pass through classification, in the same manner used in Example 1, and the content of titanium oxide present in each group was determined. The results thus obtained are listed in Table 1.

COMPARATIVE EXAMPLE 1

The same procedures used in Example 1 were repeated except that the heating by the jacket was omitted to thus prepare a rapidly soluble coating composition and to determine the solubilization time. The latter was found to be 8 minutes.

The resulting rapidly soluble coating composition was roughly divided into three groups each having the following particle size distribution: 24~30 mesh; 42~60 mesh; and 100 mesh pass through classification, in the same manner used in Example 1, and the content of titanium oxide present in each group was determined. The results thus obtained are listed in Table 1.

TABLE 1

| Ex. No. | Shaking Time | Content of Titanium Oxide (% by weight) | | | Rate of TiO$_2$ Incorporated |
|---|---|---|---|---|---|
| | | 24~30 mesh (710~500 μm) | 42~60 mesh (355~250 μm) | 100 mesh pass (≦150 μm) | |
| 1 | 20 min. | 9.7 | 10.5 | 13.4 | 12.1 |
| | 1 hr. | 9.2 | 10.0 | 13.7 | |
| 2 | 20 min. | 9.5 | 10.3 | 13.8 | 12.1 |
| | 1 hr. | 9.1 | 9.7 | 14.3 | |
| 3 | 20 min. | 10.6 | 12.2 | 14.4 | 12.1 |
| | 1 hr. | 10.2 | 11.4 | 14.7 | |
| 4 | 20 min. | 10.4 | 12.5 | 13.5 | 12.1 |
| | 1 hr. | 10.4 | 12.1 | 13.8 | |
| 5 | 20 min. | 10.2 | 12.3 | 15.6 | 12.9 |
| | 1 hr. | 10.1 | 11.5 | 16.7 | |
| 6 | 20 min. | 10.6 | 11.5 | 12.7 | 11.3 |
| | 1 hr. | 10.5 | 11.3 | 12.8 | |
| 7 | 20 min. | 6.3 | 6.6 | 7.9 | 6.5 |
| | 1 hr. | 6.0 | 6.4 | 7.7 | |
| 8 | 20 min. | 15.1 | 17.3 | 20.4 | 17.7 |
| | 1 hr. | 14.6 | 16.7 | 22.9 | |
| 1* | 20 min. | 4.6 | 8.5 | 18.0 | 12.1 |
| | 1 hr. | 3.3 | 7.6 | 25.0 | |

*Comparative Example

The data listed in Table 1 clearly indicate that the coating compositions prepared in Examples 1 to 8 each could maintain its uniform composition since the content of titanium oxide was not changed even after shaking over one hour. The coating composition of Comparative Example 1 had, at the shaking time of 20 minutes, a high content of titanium oxide in the composition whose particle size was not more than 150 μm as compared with the result of Example 1. It was confirmed that this difference was further increased when shaking was continued for one hour. This indicates that the distribution of titanium oxide in the composition was changed since the heat-treatment was omitted when preparing the coating composition.

Then, in the following Comparative Examples 2 and 3, coating compositions were prepared, while reducing the particle size of hydroxypropyl methyl cellulose as the coating base.

COMPARATIVE EXAMPLE 2

The same procedures used in Example 1 were repeated except for using 500 g of hydroxypropyl methyl cellulose (TC-5R available from Shin-Etsu Chemical Industry Co., Ltd.) having an average particle size of 50 μm and the following particle size distribution: ≧150 μm 0.4%; 106~150 μm 4.9%; 75~106 μm 10.4%; 63~75 μm 11.6%; 45~63 μm 24.4%; 38~45 μm 22.2%; and ≦38 μm 26.1% and whose viscosity as determined using a 2% by weight aqueous solution was 6 cP to thus prepare a coating composition and to determine the solubilization time thereof. The latter was found to be 21 minutes.

The resulting coating composition was roughly divided into three groups each having the following particle size distribution: 100~140 mesh; 200~235 mesh; and 330 mesh pass, through classification, in the same manner used in Example 1, and the content of titanium oxide present in each group was determined. The results thus obtained are listed in Table 2.

COMPARATIVE EXAMPLE 3

The same procedures used in Comparative Example 2 were repeated except that the heat treatment using the jacket was omitted to thus prepare a coating composition and to determine the solubilization time thereof. The latter was found to be 24 minutes.

The resulting coating composition was roughly divided into three groups each having the following particle size distribution: 100~140 mesh; 200~235 mesh; and 330 mesh pass, through classification, in the same manner used in Example 1, and the content of titanium oxide present in each group was determined. The results thus obtained are listed in Table 2.

TABLE 2

| Ex. No. | Shaking Time | Content of Titanium Oxides (% by weight) | | | Rate of TiO$_2$ Incorporated |
|---|---|---|---|---|---|
| | | 100~140 mesh (150~106 μm) | 200~235 mesh (75~63 μm) | 330 mesh pass (≦45 μm) | |
| 2* | 20 min. | 10.5 | 11.8 | 13.4 | 12.1 |
| | 1 hr. | 10.1 | 11.6 | 13.8 | |
| 3* | 20 min. | 7.6 | 10.5 | 15.5 | 12.1 |
| | 1 hr. | 4.1 | 10.0 | 21.4 | |

*Comparative Example

As shown in Table 2, it was confirmed that the coating composition of Comparative Example 2 did not cause any change in the titanium oxide distribution even after shaking for one hour and maintained its uniform composition throughout the coating composition. However, it took a longer dissolution time as compared with those observed for the coating compositions of Examples 1 to 8 since the particle size of the coating base was small on the order of 50 μm. The coating composition of Comparative Example 3 had, at the shaking time of 20 minutes, a high content of titanium oxide in the composition whose particle size was not more than 45 μm as compared with the result of Example 1. It was confirmed that this difference was further increased when shaking was continued for one hour. This indicates that the distribution of titanium oxide in the composition was altered since the heat-treatment was omitted when preparing the coating composition. The dissolution times of the compositions of these Comparative Examples were longer than those observed for the compositions of Examples 1 to 8 because of the small particle size of the coating base on the order of 50 μm.

EXAMPLE 9

There were introduced, into a high-speed stirring granulator, 500 g of hydroxypropyl methyl cellulose having an average particle size of 373 μm, the following particle size distribution: ≧1000 μm 0.6%; 710~1000 μm 4.4%; 500~710 μm 29.8%; 355~500 μm 25.2%; 250~355 μm 14.8%; 180~250 μm 6.8%; and ≦180 μm 18.4% and whose viscosity as determined using a 2% by weight aqueous solution is 6 cP and 80 g of titanium oxide (A-110 available from Sakai Chemical Industries, Ltd.). After the introduction of these ingredients, 80 g of liquid polyethylene glycol 400 (Macrogol 400; weight-average molecular weight: 380~420; available from Nippon Oil and Fats Co., Ltd.) was sprayed on the foregoing mixture with stirring for 10 minutes to give a rapidly soluble coating composition.

Purified water (188 ml) was added to an 8 oz bottle, then stirring blades were fitted to the bottle and the bottle was then immersed in a thermostatic chamber maintained at a temperature of 25° C. More specifically, at an instance when the temperature of the purified water reached 25° C., 12 g of each sample (rapidly soluble coating composition) was added to the purified water at a time while stirring at 500 rpm and the stirring operation was continued till the composition was completely dissolved therein. After the undissolved particles or agglomerates disappeared, the resulting solution was passed through a screen of 18 mesh (850 μm) and the screen was inspected for the presence of residues. The solubilization time of the composition was defined to be the time required till any residue was not observed on the screen. In this case, the solubilization time was found to be 7 minutes.

The rapidly soluble coating composition was roughly divided into 3 kinds of groups each having the following particle size distribution: 24~30 mesh; 42~60 mesh; and 100 mesh pass, through classification and the content of titanium oxide present in each group was determined. The results thus obtained are listed in Table 3. In this regard, the shaking times for the classification were 20 minutes and one hour.

EXAMPLE 10

The same procedures used in Example 9 were repeated except for using hydroxypropyl methyl cellulose having an average particle size of 504 μm, the following particle size distribution: ≧1000 μm 1.0%; 710~1000 μm 18.5%; 500~710 μm 42.5%; 355~500 μm 18.5%; 250~355 μm 7.0%; 180~250 μm 3.8%; and ≦180 μm 8.7% and whose viscosity as determined using a 2% by weight aqueous solution is 3 cP to thus prepare a rapidly soluble coating composition and to determine the solubilization time. The latter was found to be 3 minutes.

The resulting rapidly soluble coating composition was roughly divided into three groups each having the following particle size distribution: 24~30 mesh; 42~60 mesh; and 100 mesh pass through classification, in the same manner used in Example 9, and the content of titanium oxide present in each group was determined. The results thus obtained are listed in Table 3.

EXAMPLE 11

The same procedures used in Example 9 were repeated except for using hydroxypropyl methyl cellulose having an average particle size of 429 μm, the following particle size distribution: ≧1000 μm 0.4%; 710~1000 μm 14.0%; 500~710 μm 37.4%; 355~500 μm 20.6%; 250~355 μm 7.0%; 180~250 μm 4.6%; and ≦180 μm 16.0% and whose viscosity as determined using a 2% by weight aqueous solution is 15 cP to thus prepare a rapidly soluble coating composition and to determine the solubilization time. The latter was found to be 18 minutes.

The resulting rapidly soluble coating composition was roughly divided into three groups each having the following particle size distribution: 24~30 mesh; 42~60 mesh; and 100 mesh pass through classification, in the same manner used in Example 9, and the content of titanium oxide present in each group was determined. The results thus obtained are listed in Table 3.

EXAMPLE 12

The same procedures used in Example 9 were repeated except for using hydroxypropyl methyl cellulose having an average particle size of 255 μm, the following particle size distribution: ≧1000 μm 1.0%; 710~1000 μm 4.5%; 500~710 μm 11.0%; 355~500 μm 16.2%; 250~355 μm 17.9%; 180~250 μm 15.6%; and ≦180 μm 16.6% and whose viscosity as determined using a 2% by weight aqueous solution is 15 cP to thus prepare a rapidly soluble coating composition and to determine the solubilization time. The latter was found to be 15 minutes.

The resulting rapidly soluble coating composition was roughly divided into three groups each having the following particle size distribution: 24~30 mesh; 42~60 mesh; and 100 mesh pass through classification, in the same manner used in Example 9, and the content of titanium oxide present in each group was determined. The results thus obtained are listed in Table 3.

EXAMPLE 13

The same procedures used in Example 9 were repeated except for using 40 g of polyethylene glycol 600 (Macrogol 600: weight-average molecular weight 570 to 630; available from Nippon Oil and Fats Co., Ltd.) to thus prepare a rapidly soluble coating composition and to determine the solubilization time. The latter was found to be 8 minutes.

The resulting rapidly soluble coating composition was roughly divided into three groups each having the following particle size distribution: 24~30 mesh; 42~60 mesh; and 100 mesh pass through classification, in the same manner used in Example 9, and the content of titanium oxide present in each group was determined. The results thus obtained are listed in Table 3.

EXAMPLE 14

The same procedures used in Example 9 were repeated except for using 125 g of polyethylene glycol 600 (Macrogol 600: weight-average molecular weight 570 to 630; available from Nippon Oil and Fats Co., Ltd.) to thus prepare a rapidly soluble coating composition and to determine the solubilization time. The latter was found to be 5 minutes.

The resulting rapidly soluble coating composition was roughly divided into three groups each having the following particle size distribution: 24~30 mesh; 42~60 mesh; and 100 mesh pass through classification, in the same manner used in Example 9, and the content of titanium oxide present in each group was determined. The results thus obtained are listed in Table 3.

EXAMPLE 15

The same procedures used in Example 9 were repeated except for using 40 g of titanium oxide (A-110 available from Sakai Chemical Industries., Ltd.) as the pigment component to thus prepare a rapidly soluble coating composition and to determine the solubilization time. The latter was found to be 9 minutes.

The resulting rapidly soluble coating composition was roughly divided into three groups each having the following particle size distribution: 24~30 mesh; 42~60 mesh; and 100 mesh pass through classification, in the same manner used in Example 9, and the content of titanium oxide present in each group was determined. The results thus obtained are listed in Table 3.

EXAMPLE 16

The same procedures used in Example 9 were repeated except for using 125 g of titanium oxide (A-110 available from Sakai Chemical Industries., Ltd.) as the pigment component to thus prepare a rapidly soluble coating composition and to determine the solubilization time. The latter was found to be 6 minutes.

The resulting rapidly soluble coating composition was roughly divided into three groups each having the following particle size distribution: 24~30 mesh; 42~60 mesh; and 100 mesh pass through classification, in the same manner used in Example 9, and the content of titanium oxide present in each group was determined. The results thus obtained are listed in Table 3.

COMPARATIVE EXAMPLE 4

The same procedures used in Example 9 were repeated except for using 80 g of powdery polyethylene glycol 6000 (Macrogol 6000P; weight-average molecular weight 7300 to 9300, available from Nippon Oil and Fats Co., Ltd.) as the plasticizer to thus prepare a coating composition and to determine the solubilization time. The latter was found to be 8 minutes.

The resulting coating composition was roughly divided into three groups each having the following particle size distribution: 24~30 mesh; 42~60 mesh; and 100 mesh pass through classification, in the same manner used in Example 9, and the content of titanium oxide present in each group was determined. The results thus obtained are listed in Table 3.

COMPARATIVE EXAMPLE 5

The same procedures used in Example 9 were repeated except for using 15 g of liquid polyethylene glycol 400 (Macrogol 400; weight-average molecular weight 380 to 420, available from Nippon Oil and Fats Co., Ltd.) as the plasticizer to thus prepare a coating composition and to determine the solubilization time. The latter was found to be 10 minutes.

The resulting coating composition was roughly divided into three groups each having the following particle size distribution: 24~30 mesh; 42~60 mesh; and 100 mesh pass through classification, in the same manner used in Example 9, and the content of titanium oxide present in each group was determined. The results thus obtained are listed in Table 3.

COMPARATIVE EXAMPLE 6

The same procedures used in Example 9 were repeated except for using 200 g of titanium oxide (A-110 available from Sakai Chemical Industries., Ltd.) as the pigment component to thus prepare a coating composition and to determine the solubilization time. The latter was found to be 8 minutes.

The resulting coating composition was roughly divided into three groups each having the following particle size distribution: 24~30 mesh; 42~60 mesh; and 100 mesh pass through classification, in the same manner used in Example 9, and the content of titanium oxide present in each group was determined. The results thus obtained are listed in Table 3.

TABLE 3

| | | Content of Titanium Oxide (% by weight) | | | |
|---|---|---|---|---|---|
| Ex. No. | Shaking Time | 24~30 mesh (710~500 μm) | 42~60 mesh (355~250 μm) | 100 mesh pass (≦150 μm) | Rate of $TiO_2$ Incorporated |
| 9 | 20 min. | 9.2 | 10.8 | 13.2 | 12.1 |
|   | 1 hr.   | 9.0 | 10.5 | 13.7 |      |
| 10 | 20 min. | 10.1 | 11.0 | 13.1 | 12.1 |
|   | 1 hr.   | 9.9 | 10.7 | 13.3 |      |
| 11 | 20 min. | 9.8 | 11.2 | 13.4 | 12.1 |
|   | 1 hr.   | 9.1 | 11.0 | 14.0 |      |
| 12 | 20 min. | 10.2 | 12.5 | 13.0 | 12.1 |
|   | 1 hr.   | 10.2 | 12.2 | 13.9 |      |
| 13 | 20 min. | 8.9 | 10.5 | 14.3 | 12.9 |
|   | 1 hr.   | 8.5 | 10.5 | 14.5 |      |
| 14 | 20 min. | 10.8 | 12.0 | 13.0 | 11.3 |
|   | 1 hr.   | 10.1 | 11.4 | 12.8 |      |
| 15 | 20 min. | 5.3 | 6.0 | 8.4 | 6.5 |
|   | 1 hr.   | 4.9 | 6.1 | 8.6 |      |
| 16 | 20 min. | 12.9 | 16.4 | 21.7 | 17.7 |
|   | 1 hr.   | 11.9 | 15.7 | 22.0 |      |
| 4* | 20 min. | 4.6 | 8.5 | 18.0 | 12.1 |
|   | 1 hr.   | 3.3 | 7.6 | 25.0 |      |
| 5* | 20 min. | 8.4 | 10.5 | 18.2 | 13.4 |
|   | 1 hr.   | 7.9 | 9.9 | 21.7 |      |
| 6* | 20 min. | 17.4 | 21.7 | 34.9 | 25.6 |
|   | 1 hr.   | 13.3 | 20.1 | 41.3 |      |

*Comparative Example

The data listed in Table 3 clearly indicate that the coating compositions prepared in Examples 9 to 16 each could maintain its uniform composition since the content of titanium oxide was not changed even after shaking over one hour. The coating composition of Comparative Examples 4 to 6 had, at the shaking time of 20 minutes, a high content of titanium oxide in the composition whose particle size was not more than 150 μm as compared with the result of Example 9. It was confirmed that this difference was further increased when shaking was continued for one hour. This indicates that the distribution of titanium oxide in the composition of Comparative Example 4 was altered since the polyethylene glycol used as the plasticizer was in the powdery state and the weight-average molecular weight thereof was too high. In case of Comparative Example 5, this is because the amount of the liquid polyethylene glycol as the plasticizer relative to the coating base was too small. Moreover, in case of Comparative Example 6, this is because the amount of the titanium oxide as the pigment relative to the coating base was too high.

Then, in the following Comparative Examples 7 and 8, coating compositions were prepared, while reducing the particle size of hydroxypropyl methyl cellulose as the coating base.

COMPARATIVE EXAMPLE 7

The same procedures used in Example 9 were repeated except for using 500 g of commercially available hydroxypropyl methyl cellulose (TC-5R available from Shin-Etsu Chemical Co., Ltd.) having an average particle size of 50 μm and the following particle size distribution: ≧150 μm 0.4%; 106~150 μm 4.9%; 75~106 μm 10.4%; 63~75 μm 11.6%; 45~63 μm 24.4%; 38~45 μm 22.2%; and ≦38 μm 26.1% and whose viscosity as determined using a 2% by weight aqueous solution was 6 cP to thus prepare a coating composition and to determine the solubilization time thereof. The latter was found to be 22 minutes.

The resulting coating composition was roughly divided into three groups each having the following particle size distribution: 100~140 mesh; 200~235 mesh; and 330 mesh pass, through classification, in the same manner used in Example 9, and the content of titanium oxide present in each group was determined. The results thus obtained are listed in Table 4.

COMPARATIVE EXAMPLE 8

The same procedures used in Comparative Example 4 were repeated except for using 80 g of powdery polyethylene glycol 6000 (Macrogol 6000P; weight-average molecular weight 7300 to 9300, available from Nippon Oil and Fats Co., Ltd.) to prepare a coating composition and to determine the solubilization time thereof. The latter was found to be 25 minutes.

The resulting coating composition was roughly divided into three groups each having the following particle size distribution: 100~140 mesh; 200~235 mesh; and 330 mesh pass, through classification, in the same manner used in Example 9, and the content of titanium oxide present in each group was determined. The results thus obtained are listed in Table 4.

TABLE 4

| Ex. No. | Shaking Time | Content of Titanium Oxide (% by weight) | | | Rate of TiO$_2$ Incorporated |
| --- | --- | --- | --- | --- | --- |
| | | 100~140 mesh (150~106 μm) | 200~235 mesh (75~63 μm) | 330 mesh pass (≦45 μm) | |
| 7* | 20 min. | 10.2 | 11.4 | 13.6 | 12.1 |
| | 1 hr. | 9.8 | 11.0 | 13.8 | |
| 8* | 20 min. | 7.6 | 10.5 | 15.5 | 12.1 |
| | 1 hr. | 4.1 | 10.0 | 21.4 | |

*Comparative Example

As shown in Table 4, it was confirmed that the coating composition of Comparative Example 7 did not cause substantial change in the titanium oxide distribution even after shaking for one hour and maintained its uniform composition. However, it took a longer dissolution time as compared with those observed for the coating compositions of Examples 9 to 16 since the particle size of the coating base was small on the order of 50 μm. The coating composition of Comparative Example 8 had, at the shaking time of 20 minutes, a high content of titanium oxide in the composition whose particle size was not more than 45 μm as compared with the result of Example 9. It was confirmed that this difference was further increased when shaking was continued for one hour. The separation of titanium oxide was caused because the polyethylene glycol used as the plasticizer was in the powdery state and the weight-average molecular weight thereof was too high. The dissolution time of the compositions of these Comparative Examples were longer than those observed for the compositions of Examples 9 to 16 because of the small particle size of the coating base on the order of 50 μm.

What is claimed is:

1. A rapidly soluble coating composition comprising particulate hydroxypropyl methyl cellulose and/or methyl cellulose having an average particle size ranging from 200 to 1000 μm and whose content of particles having a particle size of not more than 75 μm is not more than 30% by weight, as a coating base, and 5 to 30% by weight of a plasticizer and 1 to 30% by weight of a pigment, on the basis of the weight of the coating base.

2. The rapidly soluble coating composition of claim 1 wherein the plasticizer is at least one member selected from the group consisting of polyethylene glycols which are in a solid state at ordinary temperature and have a weight-average molecular weight ranging from 950 to 25000.

3. The rapidly soluble coating composition of claim 1 wherein the plasticizer is at least one member selected from the group consisting of polyethylene glycols which are in a liquid state at ordinary temperature and have a weight-average molecular weight ranging from 190 to 630, propylene glycols, glycerin, triacetin and triethyl citrate.

4. The rapidly soluble coating composition of claim 1 wherein the viscosity of the 2% by weight aqueous solution of the coating base ranges from 2 to 60 cP.

5. The rapidly soluble coating composition of claim 1 wherein the pigment is titanium oxide and/or iron oxide.

6. A method for preparing a rapidly soluble coating composition comprising the steps of adding a plasticizer which is in a solid state at ordinary temperature and a pigment to a coating base which consists of particulate hydroxypropyl methyl cellulose and/or methyl cellulose having an average particle size ranging from 200 to 1000 μm and whose content of particles having a particle size of not more than 75 μm is not more than 30% by weight, then mixing these ingredients, and heating the mixture to a temperature of not less than the solidification point of the plasticizer.

7. A method for preparing a rapidly soluble coating composition comprising the steps of adding a pigment to a coating base which consists of particulate hydroxypropyl methyl cellulose and/or methyl cellulose having an average particle size ranging from 200 to 1000 μm and whose content of particles having a particle size of not more than 75 μm is not more than 30% by weight while spraying a plasticizer which is in a liquid state at ordinary temperature on the resulting mixture and simultaneously mixing these ingredients.

* * * * *